United States Patent [19]

Maeda

[11] 4,329,873
[45] May 18, 1982

[54] CALORIMETRIC APPARATUS
[75] Inventor: Shosaku Maeda, Atsugi, Japan
[73] Assignee: Honeywell Inc., Minneapolis, Minn.
[21] Appl. No.: 208,135
[22] Filed: Nov. 19, 1980
[30] Foreign Application Priority Data Jul. 4, 1980 [JP] Japan ............................. 55-45852

[51] Int. Cl.³ ..................... G01N 25/30; G01N 17/00
[52] U.S. Cl. ............................... 73/190 CV; 422/51; 422/95
[58] Field of Search ............... 73/190 CV; 422/51, 95, 422/97

[56] References Cited
U.S. PATENT DOCUMENTS 2,197,370  4/1940  Sullivan .................................. 73/190
3,777,562  12/1973  Clingman, Jr. ........................ 73/190

*Primary Examiner*—Herbert Goldstein
*Attorney, Agent, or Firm*—Laurence J. Marhoefer; Lockwood D. Burton; Mitchell J. Halista

[57] ABSTRACT

A calorimetric apparatus for determining the calorific content of a fuel gas uses a reactor for producing oxidation of the fuel gas and a combustion gas in the presence of a catalytic oxidizer. The oxidizer is heated by a constant current supply to a catalytic oxidation temperature. The resistance of the catalytic device is measured before and during the oxidation reaction which produces an additional heating of the catalytic device. The change in resistance is used to control a valve arranged to determine the flow rate of the fuel gas to the reactor. A display control signal is derived from a valve control signal and used to control a display for indicating the calorific content of the fuel gas.

7 Claims, 1 Drawing Figure

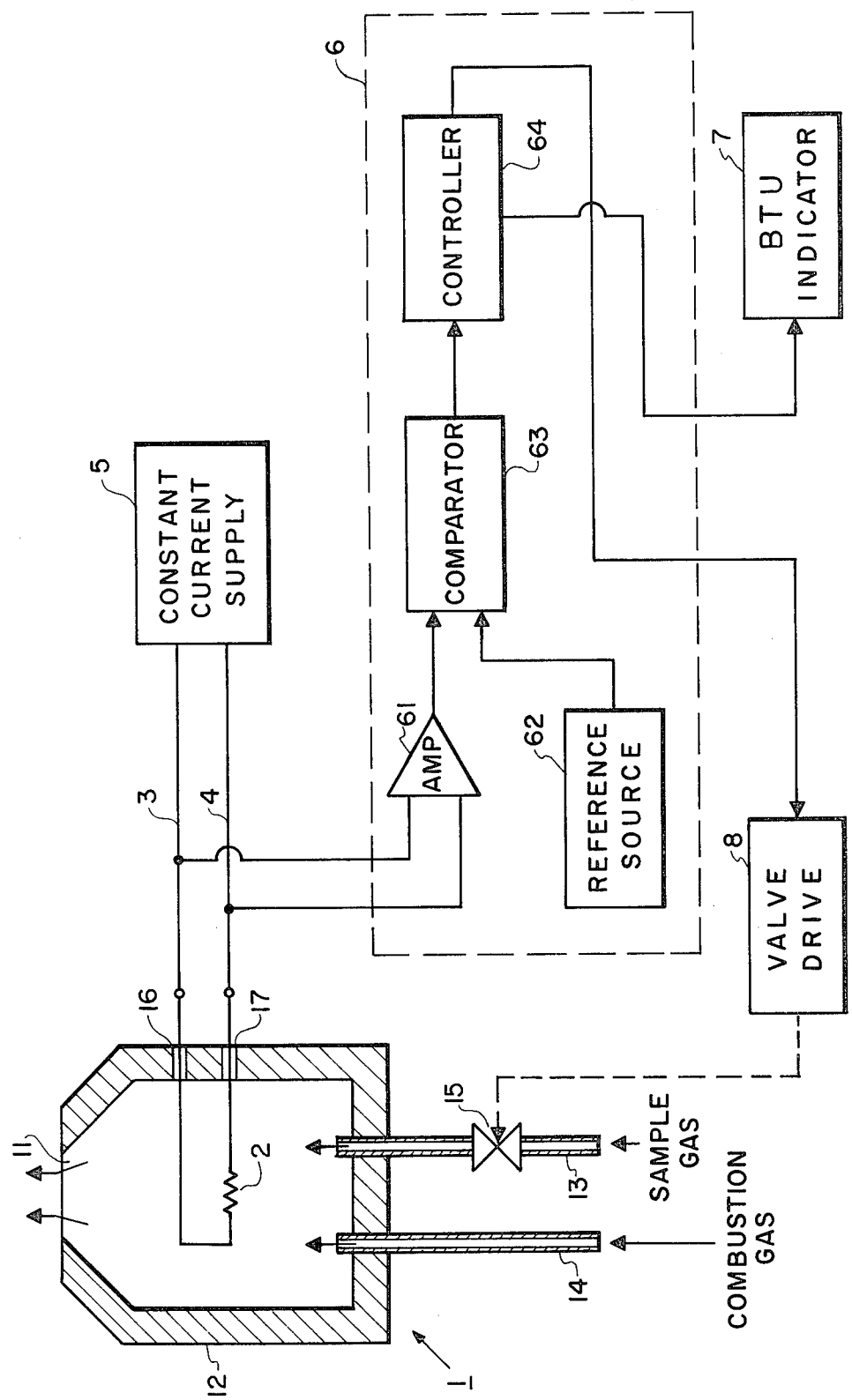

4,329,873

CALORIMETRIC APPARATUS

BACKGROUND OF THE INVENTION

1. Field of the Invention

This invention relates to a calorimetric apparatus which is suitable mainly for determining the calorific value of fuel gas.

2. Description of the Prior Art

There is a prior art apparatus known as a calorimeter which burns a predetermined quantity of gas to heat water, etc., measures the temperature of the water, etc., and compares it with the original temperature thereof, whereby the calorific value of the gas is determined. That apparatus is, however, unable to determine an accurate calorific value, since it has difficulty in completely collecting the heat generated by combustion of the gas without allowing a part of it to escape. It is also difficult to establish predetermined conditions in the combustion chamber if the apparatus is small. That apparatus does not lend itself to quick determination, since it requires a considerable time before it becomes ready to work for the purpose intended after it is placed in operation. Another disadvantage of that apparatus lies in the formation of a flame which is not desirable from the standpoint of safety or operation.

Another method known in the art employs a gas chromatograph by which the quantities of the combustible ingredients of a sample gas are analyzed, so that the total calorific value of the gas may be obtained by calculation. The use of such an apparatus is, however, very expensive.

SUMMARY OF THE INVENTION

In view of the aforementioned disadvantages of the prior art, it is an object of this invention to provide a small and inexpensive calorimetric apparatus which requires only a minor quantity of a sample gas to determine its calorific value quickly and accurately without the use of a flame for burning it, in accordance with a principle which is entirely different from those on which the prior art has been based.

According to this invention, this object is attained by an arrangement which is essentially featured by providing an electric heating element in a reactor into which sample and combustion gases are introduced, so that the sample gas may be oxidized to produce heat to cause changes in the resistance of the heating element, detecting any such change in the resistance, and transmitting a feedback control signal responsive to such resistance change to control the flow rate of the sample gas, while a display signal corresponding to the feedback control signal is also transmitted to indicate the calorific value of the sample gas.

BRIEF DESCRIPTION OF THE DRAWING

A better understanding of the present invention may be had when the following description is read in connection with the accompanying drawings, in which the single FIGURE is a schematic illustration of a calorimetric apparatus embodying an example of the present invention.

DESCRIPTION OF THE PREFERRED EMBODIMENT

The invention will now be described in further detail with reference to the single FIGURE drawing. The apparatus shown therein includes a sampling cell 1 which comprises a bottle-shaped reactor 12 having a capacity of about 50 to 100 cc, and provided at its top with an opening 11 defining a combustion products discharge passage, and a pair of gas lines 13 and 14 which define a passage for introducing a sample gas, and a passage for introducing combustion gas suitable for reacting with the sample gas, respectively, and extend into the reactor 12 through the bottom well thereof. A control valve 15 operated by a valve drive 8 is provided in the gas line 13 to control the quantity of the sample gas to be supplied into the reactor 12. An electric heating element 2 is disposed in the center of the reactor 12, and comprises a platinum wire supported on a pair of terminals 16 and 17 which are in turn supported in the side wall of the reactor 12 and electrically isolated from each other and from the reactor wall. The ends of the heating element 2 brought out through the terminals 16 and 17 are connected to a supply of a constant current 5 by lead wires 3 and 4, respectively. The supply 5 provides a constant supply of electric current to maintain the heating element 2 at a predetermined constant temperature in the range of 100° C. to 150° C.

The apparatus also includes a control system 6 which comprises an operational amplifier 61 having a pair of input terminals connected to the lead wires 3 and 4, respectively, for apply as an input there into a voltage across the terminals of the heating element 2. A reference source 62 which generates a predetermined reference voltage, a signal comparator 63 which compares the output of the operational amplifier 61 with that of the reference source 62, and an operational controller unit 64 which applies an operational process to an output signal from the comparator 63 are included in the control system 6. The operational controller unit 64 transmits a signal to the valve drive 8 which actuates the control valve 15. In addition to this feedback valve control signal, the operational controller 64 also transmits a display control signal which is proportional to the feedback valve control signal to a BTU indicator 7 which provides an analog or digital display of the calorific value of the sample gas.

In operation, a constant electric current is initially supplied from the supply 5 to the heating element 2 to maintain it at a predetermined constant temperature before gases are introduced into the reactor 12. The reference voltage in the setting unit 62 is set at the same level as an output voltage from the operational amplifier 61 during the initial operation, so that no output signal is transmitted by the comparator 63 to the controller 64.

Sample and combustion gases are then blown into the reactor 12 through the gas lines 13 and 14 to fill it with a uniform gaseous mixture. This gaseous mixture is gradually discharged through the opening 11, and the atmosphere in the reactor 12 is replaced by a fresh gaseous mixture progressively. It is appropriate to maintain a reactor atmosphere having an excess content of combustion gas, by supplying the combustion gas, for example, at a rate of 10 cc/min. in case it is oxygen, or at a rate of 50 cc/min. in case of air, for 1 cc/min. of the sample gas. In order to keep the concentration of the sample gas at its lower explosion limit, it is appropriate to correspondingly supply the combustion gas at a rate of about 200 cc/min. for 1 cc/min. of the sample gas.

When the reactor 12 is filled with the gaseous mixture, the sample gas undergoes oxidation, as a result of the platinum wire 2 serving as an oxidation catalyst. The heating element 2 is maintained at a relatively low temperature within the range of 100° C. to 150° C. as previously stated. This temperature level is not sufficiently high to cause ignition of the sample gas of the type to which this invention is applicable, but is more than sufficient to promote the catalytic action of the heating element 2 to achieve the oxidation of the sample gas. When the sample gas is concurrently brought into contact with the energized heating element 2, heat is generated by its oxidation, independently of the heat which is electrically produced. This heat of oxidation increases the electric resistance of the heating element 2, thereby raising the voltage across the terminals thereof applied by the current supply 5. In response to this increase in voltage, the comparator 63 emits a corresponding signal to the operational controller unit 64, which in turn transmits a feedback valve control signal to the valve driving unit 8. The driving unit 8 brings the control valve 15 toward its closed position to thereby reduce the flow rate of the sample gas, whereby the surface temperature of the heating element 2 is automatically controlled to a predetermined constant level. The temperature of the heating element 2 is equal to that of the electrically generated heat, plus that of the heat generated by the oxidation of the sample gas. As the electrically generated heat is maintained constant by the supply of constant electric current, the control valve 15 is actuated solely in accordance with the variation in the quantity of the heat generated by the oxidation of the sample gas.

The operational controller unit 64 produces a display signal representative of the valve control signal and expressing it in terms of calories. The display signal is transmitted to the indicating unit 7, so that the calorific value of the sample gas may be displayed. As oxidation is a reaction which is chemically equivalent to combustion, the feedback valve control signal, which is responsive to changes caused by the oxidation in the electric resistance of the heating element 2, precisely represents the calorific value of the sample gas, when it is displayed on the indicating unit 7.

Although it is generally true that the efficiency of a catalyst, i.e., the activity of a reaction which is thereby catalyzed depends on temperature, the feedback control employed for the apparatus of this invention maintains the heating element serving as a catalyst at a constant temperature, thereby ensuring a high degree of accuracy in calorific value determination with a high degree of reproducibility.

While the reactor employed in the foregoing example has been described as being in the form of a bottle having a capacity of 50 to 100 cc, it is equally possible to use a larger or smaller reactor shaped differently to provide a homogeneous mixture of the gases therein. It is also possible to provide the reactor with a cover to prevent any gaseous mixture from leaving the reactor and to thereby permit it to be agitated and mixed more effectively.

The heating element does not always need to be formed from platinum, but may also be made of any other metal belonging to Groups I, V, VI and VIII of the Periodic Table, such as copper, silver, vanadium, chromium, iron, cobalt, nickel and palladium, which may be employed alone, or in combination with any other active ingredient.

Although the embodiment as hereinbefore described has suggested equalizing the reference voltage with the output of the operational amplifier to cancel out the output of the comparator as long as the reactor does not contain any sample gas, it is alternatively possible to set the reference voltage at a desired level and detect any difference that may develop between the outputs of the comparator after introduction of the sample gas into the reactor, so that any such difference may be converted into a signal displaying the calorific value.

It is further to be noted that the changes in the electric resistance of the heating element can be detected by a conventional bridge circuit, or any other appropriate circuit.

As is obvious from the foregoing description, the calorific apparatus of this invention provides advantages which have hitherto not been obtained by prior art devices. Specifically, the calorific apparatus of the present invention is simple in construction, small in size and inexpensive to manufacture. Further, it requires only a minor quantity of sample gas, and the use of the heat produced by its oxidtion ensures very quick and accurate determination of its calorific value, since the escape of such heat minimized. As the quantity of the heat which is electrically generated on the heating element can be maintained at a constant level, an improved measuring accuracy can be obtained with a high degree of reproducibility. Finally, the absence of any flame drastically improves the safety and reliability of the operation.

Accordingly, it may be seen that there has been provided, in accordance with the present invention, an improved calorimetric apparatus.

The embodiments of the invention in which an exclusive property or privilege is claimed are defined as follows:

1. A calorimetric apparatus comprising:
   a reactor having a first passage for introducing a sample gas thereinto and a second passage for introducing combustion gas thereinto,
   a control valve provided in said sample introducing first passage,
   an oxidation catalyzing element disposed in said reactor, and adapted to be heated to a sample gas oxidation catalyzing temperature below the ignition point of the said sample gas so that said sample gas may generate heat by catalytic oxidation when brought into contact with said heating element to increase the temperature of said element,
   a control system for detecting a change in the resistance of said heating element which is caused by said heat produced by the catalytic oxidation, and for transmitting a control signal corresponding to said change to actuate said control valve to maintain said temperature of said heating element at a predetermined constant level,
   a display means connected to said control system for indicating the calorific value of said sample gas in response to said control signal.

2. A calorimetric apparatus as set forth in claim 1 wherein said oxidation catalyzing element includes a platinum coating.

3. A calorimetric apparatus as set forth in claim 1 wherein said oxidation catalyzing element includes a coating of a metal from Groups I, V, VI and VIII of the Periodic Table.

4. A calorimetric apparatus as set forth in claim 1 wherein said reactor includes a third passage for discharging gases therefrom.

5. A calorimetric apparatus as set forth in claim 1 wherein said control system includes a reference signal source for producing a reference signal corresponding to the resistance of said element when heated to said oxidation catalyzing temperature without the presence of the catalytic oxidation, comparator means for comparing said reference signal to a signal representative of the resistance of said element to produce an output signal representative of the difference therebetween and a controller means responsive to said output signal from said comparator means to produce said control signal.

6. A calorimetric apparatus as set forth in claim 5 wherein said element is electrically heated and said control system further including a constant current supply for supplying a predetermined current to said element to produce said oxidation catalyzing temperature.

7. A calorimetric apparatus as set forth in claim 6 wherein said reference signal is a voltage and said signal representative of the resistance of said element is the output voltage of said current supply.

* * * * *